United States Patent [19]

Rainsford et al.

[11] Patent Number: 5,034,379

[45] Date of Patent: Jul. 23, 1991

[54] PHARMACEUTICAL FORMULATION CONTAINING AZAPROPAZONE

[76] Inventors: Kim D. Rainsford, 18 Cline Avenue, South, Hamilton, Ontario, Canada, L8S 1W7; Michael W. Whitehouse, P.O. Box 253, Goodwood, Australia, 5034

[21] Appl. No.: 368,100

[22] Filed: Jun. 19, 1989

Related U.S. Application Data

[63] Continuation-in-part of Ser. No. 185,364, Mar. 8, 1984, abandoned, which is a continuation of Ser. No. 711,259, Mar. 7, 1985, abandoned.

[30] Foreign Application Priority Data

Mar. 8, 1984 [GB] United Kingdom ............... 8406055

[51] Int. Cl.$^5$ ..................... A61K 31/70; A61K 31/53
[52] U.S. Cl. ......................................... 514/23; 514/243
[58] Field of Search ................... 514/161, 243; 424/10

[56] References Cited

U.S. PATENT DOCUMENTS 4,440,762 4/1984 Rainsford et al. .................. 514/161

FOREIGN PATENT DOCUMENTS 0013783 6/1980 European Pat. Off. ............ 514/161

OTHER PUBLICATIONS

Rainsford, K. D., Agents and Actions 7(5-6), 573-7, (1977), "The Comparative Gastric Ulcerogenic Activities of Non-Steroidal Anti-Inflammatory Drugs".

Primary Examiner—Frederick E. Waddell
Assistant Examiner—Kevin Weddytos
Attorney, Agent, or Firm—Banner, Birch, McKie & Beckett

[57] ABSTRACT

A pharmaceutical formulation comprising azapropazone, a pharmaceutically-acceptable metabolizable carbohydrate, and a solubilizing agent which is a carboxylate of an alkali metal, alkaline earth metal, or ammonium, wherein the minimum molar ratio of carbohydrate to azapropazone is 1:1, the minimum molar ratio of carboxylate to azapropazone is 1:1, and the pH of an aqueous solution of said formulation is within the range 2 to 8.

7 Claims, No Drawings

PHARMACEUTICAL FORMULATION CONTAINING AZAPROPAZONE

This application is a continuation-in-part, of application Ser. No. 185,364, filed Mar. 8, 1984 now abandoned which is a continuation of application Ser. No. 711,259, filed Mar. 7, 1985 now abandoned This invention relates to a pharmaceutical formulation containing azapropazone.

Gastrointestinal damage (e.g., superficial lesions, ulceration and haemorrhage) is a serious side effect associated with many anti-inflammatory drugs which are used in the treatment of symptoms and pain associated with inflammatory conditions e.g. arthritis, and azapropazone also causes some of these side effects. Whereas aspirin causes ulcers in the atrium, azapropazone causes only superficial lesions in the fundus. As previously shown (Rainsford K.D. (1975) Agents and Actions, 5, 559) the gastro-intestinal damage by anti-inflammatory drugs is accentuated by fasting and by stress; conditions that often pertain when the drug is consumed, e.g. in the middle of the night to relieve pain and in the early morning to alleviate the stiffness of arthritis.

One object of the present invention is to provide a pharmaceutical formulation containing azapropazone by which damage to gastric mucosal lining can be reduced.

It is already known that the gastric mucosal damage caused by salicylates such as aspirin can be substantially reduced or eliminated by administering the drug in conjunction with an alkali metal or alkaline earth metal carboxylate and a metabolizable carbohydrate. In solution, such a mixture can be fairly strongly alkaline, owing to the dissociation of the carboxylate as a consequence of its alkaline nature, as it is a salt of a strong base and a weak acid. It is already well known that azapropazone is degraded in alkaline solution, so that alkaline solutions of azapropazone cannot be stored. The basis of the physiological actions of azapropazone, which are unknown, are clearly different from those of salicylates and most other anti-inflammatory drugs. Salicylates and most other known anti-inflammatory drugs act by suppressing prostaglandin synthesis. Prostaglandins are released by inflamed tissues and this causes the attendant symptoms of pain, swelling and temperature rise. Azapropazone is, however, known to be only a weak prostaglandin suppressor, so its relatively potent anti-inflammatory properties must be based on a different property of the drug. Also it is used as a potent uricosuric agent in low doses for the prevention of attacks of acute gout.

We have now surprisingly discovered that the gastrointestinal damage caused by azapropazone can also be substantially reduced or eliminated by administering it in conjunction with a metabolizable carbohydrate and an alkali metal salt, alkaline earth metal salt, or ammonium salt of a metabolic carboxylic acid and that the solution remains stable upon storage, provided that certain conditions are fulfilled.

According to this invention, a pharmaceutical formulation comprises azapropazone, a pharmaceutically acceptable metabolizable carbohydrate and an alkaline metal salt, alkaline earth metal salt, or ammonium salt of a metabolic carboxylic acid or precursor thereof, wherein the minimum molar ratio of carboxylate ions to azapropazone is 1:1, and the pH of an aqueous solution of said formulation is within the range of about 2 to 8, and preferably 3 to 7.

By a 'metabolic carboxylic acid' is meant one of the acids that are necessary to the efficient metabolism of intermediates resulting from the metabolism of glucose eventually to form ATP, that is those of the tricarboxylate or Krebs cycle. Examples of such salts are acetates, citrates, succinates, and oxaloacetates. Precursors of such acids can also be used: glutamates and aspartates are precursors of $\alpha$-ketoglutarates and oxaloacetates respectively, for example.

The pH of the solution must not be lower than 2 because azapropazone is also degraded under strongly acidic conditions.

Preferred metabolic carboxylates are those which do not form a too strongly alkaline aqueous solution. Salts of polybasic carboxylic acids in which not all of the labile hydrogen atoms have been replaced by metal or ammonium cations are therefore preferred, examples being disodium hydrogen citrate, monosodium dihydrogen citrate and monosodium succinate. However, provided that the previously-mentioned conditions are adhered to, salts of mono-basic metabolic acids (e.g. acetic acid) can also be used.

Glucose is the preferred metabolizable carbohydrate; other examples are sucrose, galactose, mannose, arabinose, ribose, lactose, and n-acetyl glucosamide.

More than one metabolizable carbohydrate and metabolic carboxylate salt may be included in the formulation if desired. Further, pharmaceutically acceptable excipients may be added if desired. The formulation may be prepared in solid or liquid (including dispersed) form, and, as will be demonstrated, significantly reduces the number and/or the severity of the mucosal lesions occurring in the stomach wall as compared with the same dosage of the drugs alone.

Advantages of the present invention will become clearer from a consideration of the following examples.

EXAMPLE 1

A test formulation comprising 1 part of azapropazone, 1 molar equivalent of monosodium citrate and 1 molar equivalent of D-glucose was formulated in liquid form by dissolution in a minimal amount of water. Surprisingly, the lesions index observed in the stomach of rats orally administered with the formulation of azapropazone was 0 (zero) (i.e. no damage) compared with a lesion index of 22 observed in rats treated with a like amount of azapropazone (300 mg/kg of body weight) dispersed in water. The lesion index is a measure of gastric mucosal damage (see Rainsford, 1975 Agents and Actions, 5, 533). Thin layer chromatographic analysis established that the drug contained in the aqueous solution had not undergone degradation even by up to one hour after its administration to the animals.

EXAMPLES 2 TO 9

These are set out in Table 1 and show the results of tests of azapropazone solution, and of formulations containing monosodium citrate and glucose as well as azapropazone, on rats. The number of lesions caused by the tests and the lesion index are indicated in the table. The formulations of Examples 5 and 9 are within the scope of the present invention.

Stressed rats are used in these tests to sensitize the mucosa. This allows azapropazone to cause more severe lesions (even ulcers) which are easier to detect experimentally than superficial lesion. In non-stressed animals azapropazone does not cause ulcers, at normal, pharmaceutically useful concentrations.

It is to be noted that although all of the formulations which included monosodium citrate and glucose resulted in an improved lesion index (the lower the lesion index the fewer lesions), only aqueous solutions having a pH within the specified range were stable on storage (Examples 5 and 9). The stability tests were carried out after storing samples of the aqueous solutions at 37° C. and at 50° C. for six days.

EXAMPLE 10

Blood Loss from Gastrointestinal Tract in Man as would occur if the lining of the stomach were damaged The tendencies of a pharmaceutical formulation in accordance with the invention and a commercially-available conventional azapropazone formulation (i.e. that sold under the Registered Trade Mark "Rheumox") to cause blood loss from the human gastrointestinal tract were compared.

The standard method which was employed was the radio-chromium-labelled red blood cell technique (see Dybdahl, J. H. et al., Scand. J. Gastroenterol., 15,887 1980, for methods). In this method, red blood cells are isolated from each subject, incubated with radio-active chromium ($^{51}Cr$) and reinjected into the same subject. At different time intervals afterwards faeces are collected and assayed for radio-active ($\gamma$) chromium. The intensity of radio-activity in the faeces is then related to the amount of the same isotope present in one millilitre of blood. From this the amount of blood actually present in each gram of faeces per day can be calculate. Normally a control period of about 5 to 7 days when the patient receives no drug precedes each period of about the same duration in which the patients receive the drugs under study. Aspirin is also given as a standard drug at the end of the treatment with the other drugs for this drug is well known to cause extensive bleeding from the gastrointestinal tract and therefore acts as a positive standard. The amount of bleeding (ml blood/gm faeces) caused by the drug(s) under study, less the amount of bleeding during the control period, is then divided by the corresponding bleeding caused by aspirin to derive the relative amount of blood loss caused by the drug(s) under study. These techniques are essentially non-invasive and are very sensitive in detecting gastric damage from anti-inflammatory drugs. The methods as described above were employed in an investigation to compare the blood loss into the intestinal tract in 9 healthy volunteers who took:

(1) The standard commercially available formulation of azapropazone mentioned above (Rheumox) at a dose of 1200 mg for each day for 5 days.
(2) A formulation according to the present invention in capsule form, each capsule containing azapropazone (600 mg), glucose (600 mg) and disodium hydrogen citrate (600 mg), and finally
(3) Aspirin, 1 gm each day for 4 days.

Control periods were allowed between each of the above treatments.

The results are summarized in Table 2.

TABLE 2

Summary of Specific Blood Loss Caused by the Formulation of Azapropazone According to the Invention Compared with that from Standard Rheumox and Aspirin in Human Subjects

| Drug Preparation | Blood Loss(Mean ± SD, as ml blood/gm ÷ aspirin blood loss) |
|---|---|
| Azapropazone Formulation according to the invention | 0.126 ± 0.182 (N = 9) |
| Rheumox | 0.263 ± 0.291 (N = 9) |
| Statistically significant difference (Student's "t" test), = 2.42 P 0.05. | |

The data in table 2 show that the formulation according to the present invention caused appreciably less blood loss than did the conventional azapropazone formulation (Rheumox).

EXAMPLE 11—SMALL SCALE CLINICAL TRIAL

Further confirmation of the lack of gastric side-effects from the test formulation was provided from results of a small-scale clinical trial completed in 10 patients with a proven extreme gastro-intestinal intolerance to anti-inflammatory drugs. In these patients the subjective assessment of tolerance favored the formulation of the invention in seven patients and Rheumox in two others, with one undecided. This type of trial is difficult to perform with patients who are very intolerant of anti-inflammatory drugs and the small scale of the trial was necessary on ethical grounds and hence the limited nature of the trial. However, clinical assessment has definitely favored the test formulation.

EXAMPLE 12—BIOAVAILABILITY STUDY

Bioavailability studies were performed in 4 volunteer human subjects to compare the levels in the blood (plasma) of azapropazone following oral intake of the formulation of the invention (comprising capsules of 600 mg azapropazone +600 mg each of glucose and sodium dihydrogen citrate) with that from the commercially available azapropazone capsules (Rheumox). The results showed that the two pharmaceutical preparations displayed essentially the same profile of blood levels of the drug over the main period of absorption of the drug (1–24 hours), although a slightly higher total bioavailability of the test formulation was apparent. These results show that the reduction in gastric damage and overall gastrointestinal side effects of the test formulation did not result from a reduction in the gastrointestinal absorption.

EXAMPLE 13—STABILITY TEST

The stability of the formulation of the invention has been demonstrated to be approximately equal to that of commercially available Rheumox.

TABLE 1

| Example No. | Molar proportions in Formulation Azapropazone: glucose: mono-sodium citrate | No. of Lesions | Lesion Index | Time of Test (Hours), Conditions | Stability on Storage in Aqueous Solution | pH in Aqueous Solution |
| --- | --- | --- | --- | --- | --- | --- |
| 2 | 1:0:0 | 5.4 ± 1.9 | 14.1 | 2, stressed | stable | — |
| 3 | 1:3:3 | 0.4 ± 0.4* | 1.94 | 2, stressed | unstable | 7.9 |
| 4 | 1:0:0 | 9.5 ± 3.1 | 21.0 | 24, stressed | stable | — |
| 5 | 1:1:1 | 5.3 ± 2.2* | 6.0 | 24, stressed | stable | 3.6 |
| 6 | 1:0:0 | 0.75 ± 0.8 | 3.5 | 24, arthritic rats | stable | — |
| 7 | 1:3:3 | 0* | 0 | 24, arthritic rats | unstable | 7.87 |
| 8 | 1:0:0 | 4.0 ± 1.8 | 4.0 | 24, cold stressed | stable | — |
| 9 | 1:1:1 | 1.7 ± 1.3* | 1.7 | 24, cold stressed | stable | 3.9 |

Notes:
In each case the dose of azapropazone was 300 mg/kg - i.e. 1 m.mole/Kg.
*Statistically significant reduction in the number of lesions ($P < 0.05$) using the students' t-test.

We claim:

1. A pharmaceutical formulation comprising azapropazone, a pharmaceutically-acceptable metabolizable carbohydrate, and an alkali metal salt, alkaline earth metal salt, or ammonium salt of a metabolic carboxylic acid or precursor thereof, wherein the minimum molar ratio of both carbohydrate to azapropazone and carboxylate to azapropazone is 1:1, and the pH of an aqueous solution of said formulation is within the range of about 2 to 8.

2. A formulation according to claim 1, wherein the metabolic carboxylate is a monohydrogen or dihydrogen citrate, a hydrogen succinate, or an acetate.

3. A formulation according to claim 1 or claim 2, wherein the metabolizable carbohydrate is selected from the group consisting of glucose, sucrose, galactose, mannose, arabinose, ribose, lactose, and n-acetyl glucosamine.

4. A formulation according to claim 1, wherein the molar ratio of azapropazone to sodium dihydrogen citrate to glucose is 1:1:1.

5. A formulation according to claim 1, which includes pharmaceutically-accepted excipients.

6. A stable aqueous solution of a formulation according to claim 1 having a pH in the range of about 2 to 8.

7. A stable aqueous solution of a formulation according to claim 6 and having a pH in the range 3 to 7.

* * * * *